(12) United States Patent  
Riva

(10) Patent No.: US 7,891,977 B2  
(45) Date of Patent: Feb. 22, 2011

(54) APPARATUS FOR ENDODONTIC TREATMENT BY CIRCULATION OF ENZYMATIC SOLUTIONS IN THE PULP CAVITY AND IN THE ROOT CANALS

(75) Inventor: Ermete Riva, Merate (IT)

(73) Assignee: Helvodont Limited, Dublin (IE)

( * ) Notice: Subject to any disclaimer, the term of this patent is extended or adjusted under 35 U.S.C. 154(b) by 389 days.

(21) Appl. No.: 12/063,681

(22) PCT Filed: Nov. 21, 2005

(86) PCT No.: PCT/IT2005/000677

§ 371 (c)(1),
(2), (4) Date: Feb. 13, 2008

(87) PCT Pub. No.: WO2007/052317

PCT Pub. Date: May 10, 2007

(65) Prior Publication Data

US 2008/0280252 A1    Nov. 13, 2008

(30) Foreign Application Priority Data

Oct. 31, 2005   (IT) .......................... MI2005A2076

(51) Int. Cl.
*A61C 5/02* (2006.01)

(52) U.S. Cl. ........................................ 433/81; 433/224

(58) Field of Classification Search .................. 433/81, 433/224, 229; 604/4.01, 6.11, 6.13, 6.15, 604/7
See application file for complete search history.

(56) References Cited

U.S. PATENT DOCUMENTS

| 4,993,947 | A | * | 2/1991 | Grosrey ........................ 433/81 |
| 5,387,517 | A | | 2/1995 | Cini |
| 6,162,202 | A | * | 12/2000 | Sicurelli et al. ............. 604/272 |
| 6,971,878 | B2 | * | 12/2005 | Pond ............................ 433/81 |
| 2005/0112525 | A1 | | 5/2005 | McPherson et al. |
| 2005/0170312 | A1 | * | 8/2005 | Pond ............................ 433/81 |
| 2005/0180929 | A1 | | 8/2005 | Lynch et al. |

FOREIGN PATENT DOCUMENTS

DE    196 22 195 A1    12/1996
WO    81/01242 A    5/1981

* cited by examiner

*Primary Examiner*—Cris L Rodriguez
*Assistant Examiner*—Hao D Mai
(74) *Attorney, Agent, or Firm*—Young & Thompson

(57) ABSTRACT

An apparatus is described, for endodontic treatment, whereby the operations for complete removal of connective, vascular and nervous tissues in the pulp cavity and in the root canals can be automatically carried out by chemical and pharmacological disintegration and by employing suitable enzymatic solutions such as trypsin at various degrees of dilution. The use of positive-displacement pumps guarantees that precise quantities of the chemical substances are used in the stages of emptying, disinfection, washing, drying and final filling of the root canals and of the pulp cavity. Temperature control of the fluids in circulation ensures that reaction times of the chemical substances used can be repeated at each cycle.

30 Claims, 2 Drawing Sheets

Figure 5:
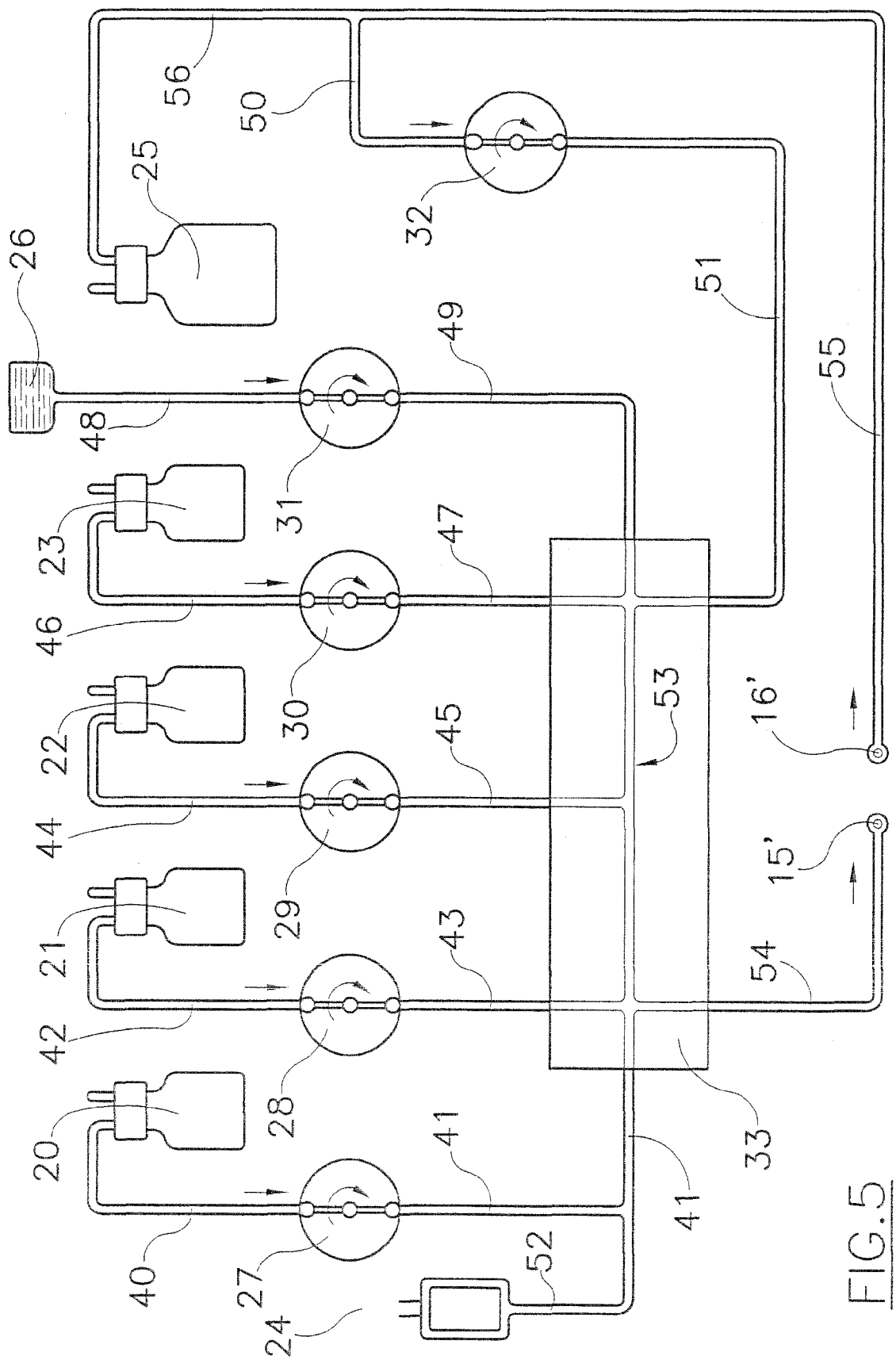

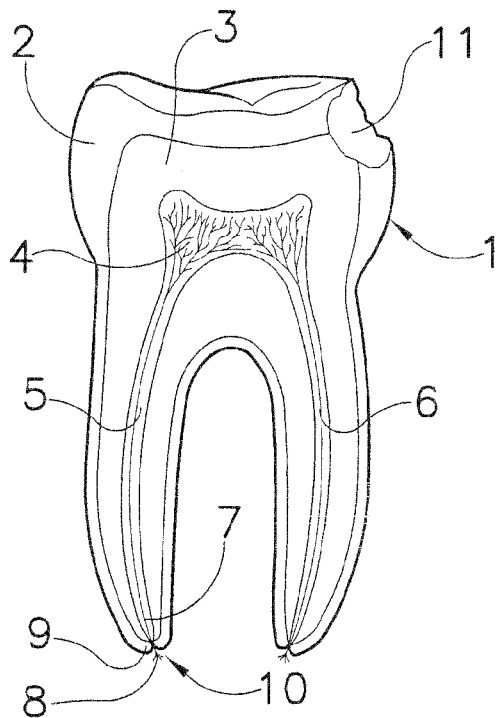
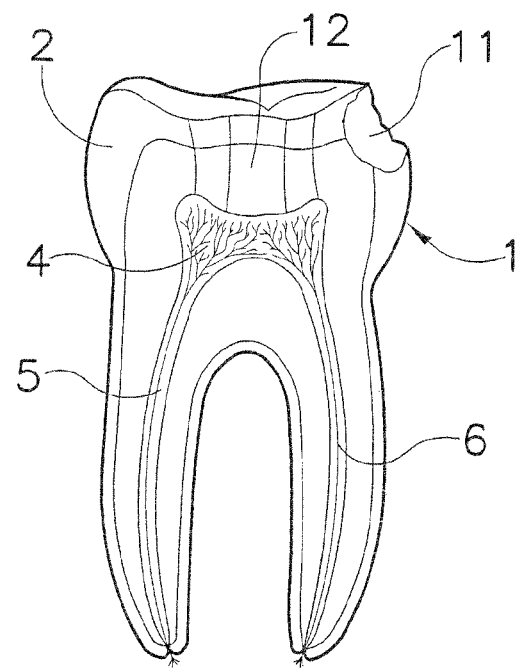
FIG.1　　　　　　　FIG.2
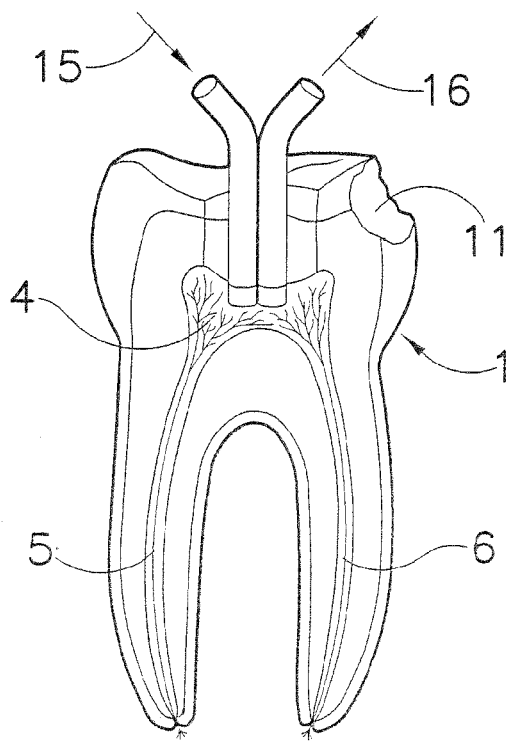
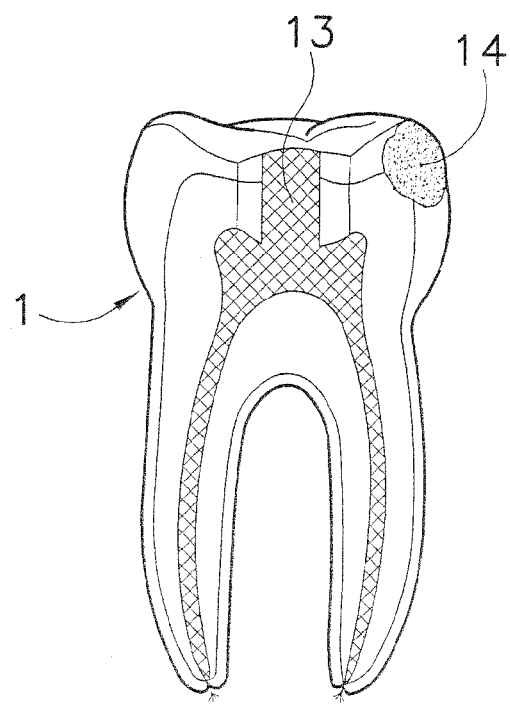
FIG.3　　　　　　　FIG.4

APPARATUS FOR ENDODONTIC TREATMENT BY CIRCULATION OF ENZYMATIC SOLUTIONS IN THE PULP CAVITY AND IN THE ROOT CANALS

FIELD OF APPLICATION OF THE INVENTION

The present invention relates to medical equipment for dental use, and in particular to an apparatus for endodontic treatment by means of which enzymatic solutions are caused to circulate in the pulp cavity and in the root canals. To clarify the operative sphere of this type of dental equipment, FIG. 1 shows a dissected perspective of a premolar 1 with crown 2, dentine 3, pulp cavity 4, root canals 5 and 6 and apical foramen 7 into which a bundle of nerves 8 with artery 9 and vein 10 penetrate, terminating in the pulp cavity 4. A decayed area 11 can be seen on the crown 2 and this must be removed before the missing part of the crown can be re-built. If there is a lesion to the dental pulp in a live tooth, endodontico treatment (commonly known as devitalization) must be carried out using rotating instruments (milling cutters) to open up the crown and enter the pulp cavity. In the case of an apical granuloma or of repeated endodontic treatment, the tooth is no longer live and devitalization is therefore unnecessary but further cleansing of the pulp cavity and of the root canals must be done (FIG. 2). Details of FIG. 3 will be given in the description of the invention as a whole. FIG. 4 shows how the tooth 1 looks when the work has been completed, namely after devitilization, cleaning and closure of the root canals and pulp canal. As will be seen in FIG. 4, the central hole 12 has been filled in with sealing material 13 and the part of the crown that was removed to clean out the decayed material has been rebuilt with a special resin 14.

PRESENT STATE OF THE ART

According to conventional methods, when devitalizing a tooth a special type of instrument is inserted into the root canals and is suitably moved about to remove the pulp contained therein. Difficulties arise on account of the internal shape of the roots and X-rays are needed, though today less than formerly since electronic devices now exist for measuring the length of the root canals. The method that uses electricity at high frequency is no longer recognised as scientifically valid and acceptable. International literature on the subject is so inadequate as to be almost non-existent.

The U.S. Pat. No. 5,046,950 describes an apparatus (and a method) for devitalizing a tooth and for applying treatment to the dental root canals by the use of certain inorganic chemical solutions. Generally speaking this method comprises the following steps: a) a sealed vacuum receptacle is fitted to the pulp cavity and root canals; b) the chemical solutions are run into the pulp cavity and into the root canals, one after another and are taken from a series of bottles maintained at atmospheric pressure; c) said inorganic solutions are sucked up into the vacuum receptacle when they have served their purpose; d) a sealing solution is applied to the treated parts. In addition to these stages, the vacuum level is varied 40 times per minute to assist aspiration of the pulp. Just because of this, the treatment is not entirely bereft of mechanical actions; these, however, are not carried out by hand but by repeated pressure/depression pulses applied to the liquid inside the pulp cavity. Compared with previous methods, in this one no manual action is required on the tooth apart from that strictly necessary for inserting the cannulae in position and removing them after use, but this method does require a highly complex apparatus that functions by means of a number of hydraulic electric valves. One drawback connected with the use of hydraulic electric valves for activating aspiration of solutions inside the root canals, is the difficulty of taking up the precise quantity of liquid from the bottles during the instant when an electric valve is opened, typically 200 ms.

Another element of uncertainty consists in having to consider the dead spaces in the hydraulic circuit inside the electric valves. What happens in practice is that, at each opening, the pulp cavity is flooded with a stream of liquid, part of which is not used and is therefore wasted.

Another technical problem related to the use of inorganic chemical reagents in aqueous solutions that carry out their destructive effect by alterations in the pH (for example potassium hydrate), is that the solutions can drip out through the apical foramen in the root canals and invade the surrounding tissues (gums, nerves, blood vessels), damaging them to such an extent that they may never recover. One way of preventing this trouble is to stop the devitalizing process immediately it is completed and no later, but we have seen that, with presently-known equipment, this is impossible because of inaccuracies that arise over using the right amount of reagent and in knowing how long it takes to secure a reaction when the reagent is in contact with the pulp. Another way of limiting the difficulty, concomitant with the first, is to experiment with the use of different types of chemical reagents that are less harmful to the surrounding tissues.

PURPOSE AND SUMMARY OF THE INVENTION

Purpose of the present invention it to secure a precise control over the quantities of reagent administered, and over the time they have to remain in contact with the pulp.

A further purpose is to limit the harm done to the surrounding tissue caused by part of the reagent dripping out through the apical foramen in the root canals.

The invention achieves its set purpose by means of an apparatus for endodontic treatment, as described in claim 1. Further advantageous characteristics possessed by the apparatus are described in the dependent claims. Contrary to what happens with equipment already known to the art, the apparatus produced by this invention does not make use of vacuum sealed aspiration to recall the liquid reagents and washing solutions in the pulp cavity, neither does it use electric valves in the hydraulic circuit to vary the shape of the cavity in accordance with the various stages of treatment.

The apparatus here described includes positive-displacement pumps, preferably peristaltic pumps, along the paths of fluid flow to and from the pulp cavity and root canals. The chemical solutions to be used are contained in bottles open to the air and therefore at room pressure. As is well-known, the delivery of positive-displacement pumps is calculated during the design stage of production. In peristaltic pumps delivery depends on the speed of rotation and on the volume of the flexible tube the shape of which chances at each cycle; further, when idle, their outflow connection remains closed. By using this type of pump the quantities of substances to be used during the devitalizing stages can be accurately proportioned and needless waste avoided. Control of the time the reagent takes to react when in contact with the pulp is obtained by keeping the temperature of the aqueous solution of reagent used at the desired level for the whole time it is in circulation. One preferred form of realization employs a small metal block for hydraulic circulation heated electrically and temperature-regulated by a thermostat. In another form, less advisable on account of the greater amount of heat used, temperature of the reagent in the bottle is adjusted by a thermostat. A second positive-displacement pump is used for washing out the tooth cavity with a neutral solution at the end of its operative cycle. By a combination of means employed (displacement pump plus thermostat for the fluid) the precise quantity of reagent can be taken from the respective bottles and be kept in circulation for a length of time calculated according to the type of reagent, and to the shape and size of the tooth being treated. Details of times and quantities of reagents and washing solutions can be stored in the microprocessor's memory.

In conclusion, adoption of positive-displacement pumps makes possible the use of small quantities of pure high-quality (and therefore costly) reagents, calculating the minimum indispensable for each type of tooth and, apart from exceptional cases, completing the devitalizing process in a single operation. The control maintained over temperature of the fluids in circulation ensures that reaction times of the chemical substances can be repeated for each operation.

The constructional and functional characteristics of the apparatus subject of the invention are well suited to the various stages of the dental devitalizing process based on the use of enzymes able to separate the connective material (e.g. trypsin, pepsin, papain, etc.). The use of enzymes instead of inorganic substances with a caustic effect that are employed in known methods, considerably reduces any damage to surrounding tissues if the fluid drips through the apical foramen in the root canals, since the pH remains substantially neutral.

SHORT DESCRIPTION OF THE FIGURES

Further purposes and advantages of the present invention will be made clear by the following detailed description of one already realized example and by the attached drawings, supplied for explanatory purposes only, and in no way limitative, in which:

FIG. 1, already described, shows a premolar tooth with decayed part dissected longitudinally.

FIG. 2, already described, shows the tooth in FIG. 1 after preparing the cavity to secure access to the root canals.

FIG. 3 shows the tooth in FIG. 2 after insertion of an entry and exit head for the fluids used by the invented apparatus for devitalizing and treatment.

FIG. 4, already described, shows the tooth after devitalization and filling.

FIG. 5 shows a diagram of how the hydraulic circuit functions in the apparatus for endodontic treatment subject of the present invention.

DETAILED DESCRIPTION OF SOME PREFERRED EMBODIMENTS FOR REALIZING THE INVENTION

With reference to FIG. 3, it will be seen that a small head consisting of two stainless steel tubes 15, 16 has been fitted into the hole 12 (FIG. 2), the first of these tubes being used to let fluid (liquid or air) into the pulp cavity 4 and into the root canals 5, 6 while the second tube is used for fluid outflow. The hydraulic diagram in FIG. 5 represents an apparatus for endodontic treatment, said apparatus being connected to two tubes 15 and 16 (FIG. 3) by two flexible tubes (not shown) joined to two connections 15' and 16'. The electrical part is not shown either for the sake of simplicity, but this can in any case be added by an expert in electronics in accordance with the following explanations and using parts available on the market. With reference to FIG. 5, the hydraulic circuit comprises: 5 bottles for liquids 20, 21, 22, 23, and 25 each having a stopper in which a first hole is made for a short length of tube in communication with the environment, and a second hole made for another tube forming part of the hydraulic circuit. Bottles 20, 21, 22 and 23 contain the products used during endodontic treatment, while bottle 25 is used for collecting waste liquid.

When described in detail:

bottle 20 contains a solution of inorganic salts for washing purposes;

bottle 21 contains the reagent consisting of an aqueous solution, trypsin for example, diluted approximately between 1:10 and 1:20 by weight. Other proteolytic enzymes can be used either singly or combined.

bottle 22 contains a disinfecting solution;

bottle 23 contains a dense solution for filling the dental cavity.

The diagram shows six peristaltic pumps 27, 28, 29, 30, 31 and 32; a hydraulic circulation manifold 33, a pressure transducer 24 and an air filter 26. The manifold 33 is a small block of stainless steel inside which are seven points of connection among respective parietal apertures and a duct 53 common to all. Bottles 20, 21, 22, 23 and connected to pump inlets 27, 28, 29, 30 by their respective tubes 40, 42, 44 and 46. The pump outlets 27, 28, 29 and 30 are connected to a similar number of inlets to the manifold 33 by respective tubes 41, 43, 45 and 47. The pressure transducer 24 is connected to an inlet to the manifold 33 through a tube 52. The air filter 26 is connected to the pump inlet 29 through a tube 48, while the outlet from said pump is connected to an inlet to the manifold 33 through a tube 49. Another inlet to the manifold 33 is connected to the pump outlet 32, entry being connected to a tube 50 that divides forming two more tubes 55 and 56, the first of which is joined to connection 16' and the second to the large bottle 25 for waste liquid. The only outlet from the manifold 33 is joined to connection 15' through a tube 54.

As regards operating the device, the manifold block 33, fitted with a thermal sensor (not shown in the figure), is kept at a constant temperature of about 40° C. by a heater controlled by a thermo-regulating electronic circuit that reads the temperatures measured by the thermal sensor. The pressure transducer 24 connected to the manifold block 33 on a branch of the pump 27, measures pressure in the hydraulic circuit. At the position of each bottle 20, 21, 22 and 23, there is a detector of the minimum permitted level and at the position of bottle 25 is a detector of the maximum permitted level. Data is collected by a microprocessor and passed on to the program controlling the apparatus. Described in greater detail, pressure measurement is used to turn off the positive-displacement pumps if pressure in the hydraulic circuit is found to be too high. Temperature measurements are used for adjusting the thermostat; more details will be given further on. As all the bottles are open to the environment through the hole in the stopper, when idle all the hydraulic circuits upstream and downstream of the pumps are subjected to atmospheric pressure. When all the pumps are idle they impede circulation of fluid, air included, and function as closed valves.

To make the apparatus safer, all circuits are fed by a 12V rated accumulator battery. No live part on mains voltage can come in contact with the dentist or with the patient. Mains electricity (85-265 V) is connected to a transformer with double insulation; this part, with its buffer battery-charged feeder, is situated in an inner container kept isolated and mechanically separate from the low-voltage circuits. The apparatus can function for at least ten hours without mains electricity so that if a blackout occurs when the operation is in progress, it can be concluded in complete safety. The patient is therefore protected from any harm that might arise from a prolonged presence of chemical substances in the dental cavity, since the apparatus automatically concludes every operation with a washing stage, even if the dentist is not present. Further, the measuring means for the level of liquid in the bottles prevents a fresh cycle from starting if the level in any of the bottles 20, 21, 22, 23 shows an amount sufficient for only two cycles.

If however the level falls below the minimum, this in no way prevents the cycle in progress from being completed.

Here follows a description of an endodontic treatment including one of devitilization executed with the apparatus in FIG. 5. The treatment consists of the following steps.

1. Having fitted the head with steel tubes 15 and 16 inside the aperture 12 made in the crown of the tooth, and sealed it, and having joined up the head with the flexible tubes (not shown) to connections 15' and 16', the most suitable program for the type of tooth concerned is selected from among those stored in the microprocessor's memory.
2. The pump 27 is turned on for about 4 seconds to take about 4 cm$^3$ of solution from bottle 20. If during this operation the pressure transducer 24 indicates a pressure of, or greater than, 200 kPa (absolute), the pump 27 stops and a signal of obstruction in the hydraulic circuit is given; if not, connection to the tooth 1 is considered as perfect and the operation proceeds.
3. Pump 28 is turned on for about 5 seconds and pump 32 for a time varying between 1 and 60 minutes, according to the shape of the tooth to be treated. This permits the internal and external hydraulic circuit to be completely filled together with the tubes 41 and 52, the hollow part in the manifold block 33, tube 54, the external flexible tubes, the head 15, 16, the first part of the pulp cavity in the tooth 1, and the tubes 55, 50 and 51. During the time programmed for rotation of the pump 32, the reagent taken from bottle 21 is injected into the pulp cavity and again circulated in the cavity inside the manifold block 33, in this way quickly acquiring the temperature programmed for heat exchange with the internal parts. By operating in this way at a constant temperature (close to body temperature), over 80% of the liquid taken from the bottle can be used, bringing it in a highly turbulent state in contact with the organic material contained in the pulp cavity and obtaining an excellent degree of penetration inside the roots.
4. While the pump 32 continues to function, the pump 31 is turned on for 15 seconds during which it draws in air from its surroundings through the filter 26. This causes pressure to rise in the ducts leading to the manifold 33 and facilitates expulsion of the liquids contained which are then conveyed to the waste discharge bottle 25. The sensor of maximum level reached in the bottle 25, stops both pumps 32 and 31 until the bottle has been replaced. This step, which may be called drainage, always precedes a subsequent washing step and both are repeated to bring the internal and external hydraulic circuits, including the dental cavity (consisting of the emptied pulp cavity and root canals) to a condition of chemical neutrality (equivalent to the neutral pH of the solution of inorganic salts).
5. The succession of events, from the start of the washing step, is as follows:
    the second pump 27 is started up to run for about 9 seconds to take a previously set quantity of inorganic salts solution from bottle 20;
    pump 32 is started from when pump 27 stops, and runs for 20 seconds;
    emptying pump 31 is started from when pump 27 stops, and runs for 20 seconds.
    Overall time for the three events is about 29 seconds, but this is only approximate and can change according to the delivery of the pumps in use or to the diameters of the relative ducts in the hydraulic circuit.
6. This step is the same as the second, except that pump 29 is used instead of pump 28; in this way the liquid contained in bottle 22 can be used to finish emptying the pulp cavity and the root canals in tooth 1, or else to disinfect it. Operating time for recirculating pump 32 can be programmed between 1 and 60 minutes irrespective of the time interval chosen for the second step described in point 2.
7. The drainage step 4 and washing step 5 are repeated chiefly in order to return the dental cavity to a condition of chemical neutrality.
8. If the particular shape of the tooth, especially the complex nature of root anatomy, makes necessary further chemical action for complete and certain removal of the pulp tissue right as far as the apical area, at the end of each washing step 5, steps 2 and 6 can be repeated taking the required reagents from bottle 20 or from bottle 21 respectively. The programmes for these exceptional cycles are stored in the microprocessor's memory.
9. The dental cavity is dried before inserting the filling material and consolidating it. To do this pumps 31 and 32 are started up and temperature of the manifold block 33 is raised to permit faster evaporation of the remaining fluid contained in the hydraulic circuit. Air from the surrounding environment is drawn in through the filter 26, passed through the heated block 33 and then into the dental cavity through the external circuit joined to connections 15' and 16'. Part of the air is again circulated by pump 32 and partly expelled through the aperture in the stopper of bottle 25. This stage can be programmed to last from 0 to 60 minutes.
10. This step is devoted to tilling the cavity in the tooth (a volume equivalent to that of the pulp cavity and root canals now emptied). Pump 30 is started up and takes from bottle 23 the substance chosen for this operation which is carried out in the same way as an additional washing stage but only if the substance chosen for closing and sealing the dental cavity, as it is at the end of the preceding step, is sufficiently fluid and soluble. If not, for denser or non-soluble substances, use is made of an external package, a set of which are at connection 15', containing a suitable quantity of sealing substance. In this case pump 31 is started up to compress the air in the duct 54; the pressure level read by the transducer 24 will be adjusted by pump 31 according to the viscosity of the substance and the amount to be used. If this substance should be insoluble, whenever any filling has to be done it will be sufficient to replace the external tubes on the apparatus.

The invention claimed is:
1. An apparatus for endodontic treatment, comprising:
a hydraulic circuit (28, 32, 33) for facilitating circulation of medical solutions within a pulp cavity (4) and root canals (5,6) of a tooth (1) to be treated, said hydraulic circuit including
a first positive-displacement pump (28) connected to a first containing means (21) containing, at atmospheric pressure, a first medical solution,
a second positive-displacement pump (32) for recirculation of fluids put into said hydraulic circuit (33), a third positive-displacement pump (31) to pump an aeriform fluid within said hydraulic circuit (33), a means for thermostatic regulation of the temperature of fluids circulating within said hydraulic circuit (33), a means for controlling an activation sequence and operative times of said positive-displacement pumps (28, 31, 32), operated by a memory-stored program configured for the tooth to be treated, and a second containing means at atmospheric pressure (25) fitted with a maximum-level sensor connected to said controlling means, the second containing means being connected to said second positive-displacement pump (32) for collecting waste liquid and partly expelling said aeriform fluid.

2. The apparatus as in claim 1, wherein said hydraulic circuit includes a manifold means (33) internally channeled and electrically heated by said means for thermostatic regulation.

3. The apparatus as in claim 1, further comprising:
a means (24) for measuring the pressure in said hydraulic circuit (33) connected to said controlling means.

4. The apparatus as in claim 1, further comprising:
a fourth positive-displacement pump (27) connected to a third containing means at atmospheric pressure (20) containing a second medical solution.

5. The apparatus as in claim 4, further comprising:
a fifth positive-displacement pump (29) connected to a fourth containing means at atmospheric pressure (22) containing a third medical solution.

6. The apparatus as in claim 5, further comprising:
a sixth positive-displacement pump (30) connected to a fifth containing means at atmospheric pressure (23) containing a fourth medical solution.

7. The apparatus as in claim 4, wherein said first, second, and third containing means at atmospheric pressure are each fitted with a minimum-level sensor connected to said controlling means.

8. The apparatus as in claim 1, wherein said first, second, and third positive-displacement pumps are peristaltic type pumps.

9. The apparatus as in claim 1, wherein said first and second containing means at atmospheric pressure are bottles provided with stoppers, perforated to communicate with said hydraulic circuit (33) and further perforated to communicate via a tube with the external environment.

10. The apparatus as in claim 1, wherein said first medical solution includes a reagent.

11. The apparatus as in claim 4, wherein the pH of said second medical solution is neutral.

12. The apparatus as in claim 5, wherein said third medical solution is a disinfectant.

13. The apparatus as in claim 6, wherein said fourth medical solution includes a substance for filling and consolidation.

14. The apparatus as in claim 1, wherein said first containing means at atmospheric pressure (21) is fitted with a minimum-level sensor connected to said controlling means.

15. The apparatus as in claim 5, wherein said first, second, third, and fourth containing means at atmospheric pressure are each fitted with a minimum-level sensor connected to said controlling means.

16. The apparatus as in claim 6, wherein said first, second, third, fourth, and fifth containing means at atmospheric pressure are each fitted with a minimum-level sensor connected to said controlling means.

17. The apparatus as in claim 2, wherein said first, second, and third positive-displacement pumps are peristaltic type pumps.

18. The apparatus as in claim 3, wherein said first, second, and third positive-displacement pumps are peristaltic type pumps.

19. The apparatus as in claim 4, wherein said first, second, third, and fourth positive-displacement pumps are peristaltic type pumps.

20. The apparatus as in claim 5, wherein said first, second, third, fourth, and fifth positive-displacement pumps are peristaltic type pumps.

21. The apparatus as in claim 6, wherein said first, second, third, fourth, fifth, and sixth positive-displacement pumps are peristaltic type pumps.

22. The apparatus as in claim 7, wherein said first, second, third, and fourth positive-displacement pumps are peristaltic type pumps.

23. The apparatus as in claim 14, wherein said first, second, and third positive-displacement pumps are peristaltic type pumps.

24. The apparatus as in claim 2, wherein said first and second containing means at atmospheric pressure are bottles provided with stoppers, perforated to communicate with said hydraulic circuit (33) and further perforated to communicate via a tube with the external environment.

25. The apparatus as in claim 3, wherein said first and second containing means at atmospheric pressure are bottles provided with stoppers, perforated to communicate with said hydraulic circuit (33) and further perforated to communicate via a tube with the external environment.

26. The apparatus as in claim 4, wherein said first, second and third containing means at atmospheric pressure are bottles provided with stoppers, perforated to communicate with said hydraulic circuit (33) and further perforated to communicate via a tube with the external environment.

27. The apparatus as in claim 5, wherein said first, second, third, and fourth containing means at atmospheric pressure are bottles provided with stoppers, perforated to communicate with said hydraulic circuit (33) and further perforated to communicate via a tube with the external environment.

28. The apparatus as in claim 6, wherein said first, second, third, fourth, and fifth containing means at atmospheric pressure are bottles provided with stoppers, perforated to communicate with said hydraulic circuit (33) and further perforated to communicate via a tube with the external environment.

29. The apparatus as in claim 7, wherein said first, second, and third containing means at atmospheric pressure are bottles provided with stoppers, perforated to communicate with said hydraulic circuit (33) and further perforated to communicate via a tube with the external environment.

30. The apparatus as in claim 14, wherein said first and second containing means at atmospheric pressure are bottles provided with stoppers, perforated to communicate with said hydraulic circuit (33) and further perforated to communicate via a tube with the external environment.

* * * * *